United States Patent [19]

Polaschegg

[11] Patent Number: 5,230,341
[45] Date of Patent: Jul. 27, 1993

[54] MEASURING THE CHANGE OF INTRAVASCULAR BLOOD VOLUME DURING BLOOD FILTRATION

[75] Inventor: Hans-Dietrich Polaschegg, Oberursel, Fed. Rep. of Germany

[73] Assignee: Fresenius AG, Fed. Rep. of Germany

[21] Appl. No.: 660,240

[22] Filed: Feb. 25, 1991

Related U.S. Application Data

[63] Continuation of Ser. No. 380,218, Jul. 14, 1989, abandoned.

[30] Foreign Application Priority Data

Aug. 13, 1988 [DE] Fed. Rep. of Germany ....... 3827553

[51] Int. Cl.$^5$ .............................................. A61B 5/00
[52] U.S. Cl. ........................................ 128/668; 604/5
[58] Field of Search ................ 128/668, 691; 604/4–6, 604/27, 29–31, 65, 251, 253, 255

[56] References Cited

U.S. PATENT DOCUMENTS

| | | | |
|---|---|---|---|
| 3,964,479 | 6/1976 | Boag et al. | 604/5 X |
| 4,353,368 | 10/1982 | Slovak et al. | 604/5 |
| 4,432,231 | 2/1984 | Napp et al. | 604/253 X |
| 4,797,655 | 1/1989 | Orndal et al. | 604/31 X |

FOREIGN PATENT DOCUMENTS

| | | |
|---|---|---|
| 0018817 | 11/1980 | European Pat. Off. ............ 604/253 |
| 0089003 | 9/1983 | European Pat. Off. . |
| 3640089 | 6/1988 | Fed. Rep. of Germany . |

OTHER PUBLICATIONS

R. N. Greenwood, et al., "Serial blood water estimations and in-line blood fiscometry: the continuous measurement of blood volume during dialysis procedures", Clinical Science (1984) 66, 575–583.

U. Schallenberg, et al., "A New Method of Continuous Haemoglobinometric Measurement of Blood Volume During Haemodialysis", Life Support Systems (1987), 5, 293–305.

E. L. Bradley, III, M. D. et al., "The Velocity of Ultrasound in Human Blood under Varying Physiologic Parameters", Journal of Surgical Research, (1972), 12, 290–297.

K. Kirk Shung, Ultrasonic Characterization of Blood, vol. II, Chapter 10, 227–242 1986.

*Primary Examiner*—Ruth S. Smith
*Attorney, Agent, or Firm*—Andrus, Sceales, Starke & Sawall

[57] ABSTRACT

To determine in simple manner the change of the intravascular blood volume during filtration, in the extracorporeal blood circuit (2) of a blood purification apparatus at least one ultrasonic sensor (15) is arranged which is connected to an evaluating unit (18) which is configured in such a manner that at the start of the filtration a first ultrasonic signal is stored and during the filtration the change of the ultrasonic signals is determined. From the change of the ultrasonic signals the change of the hematocrit is determined and from this the change of the intravascular blood volume is deduced.

9 Claims, 1 Drawing Sheet

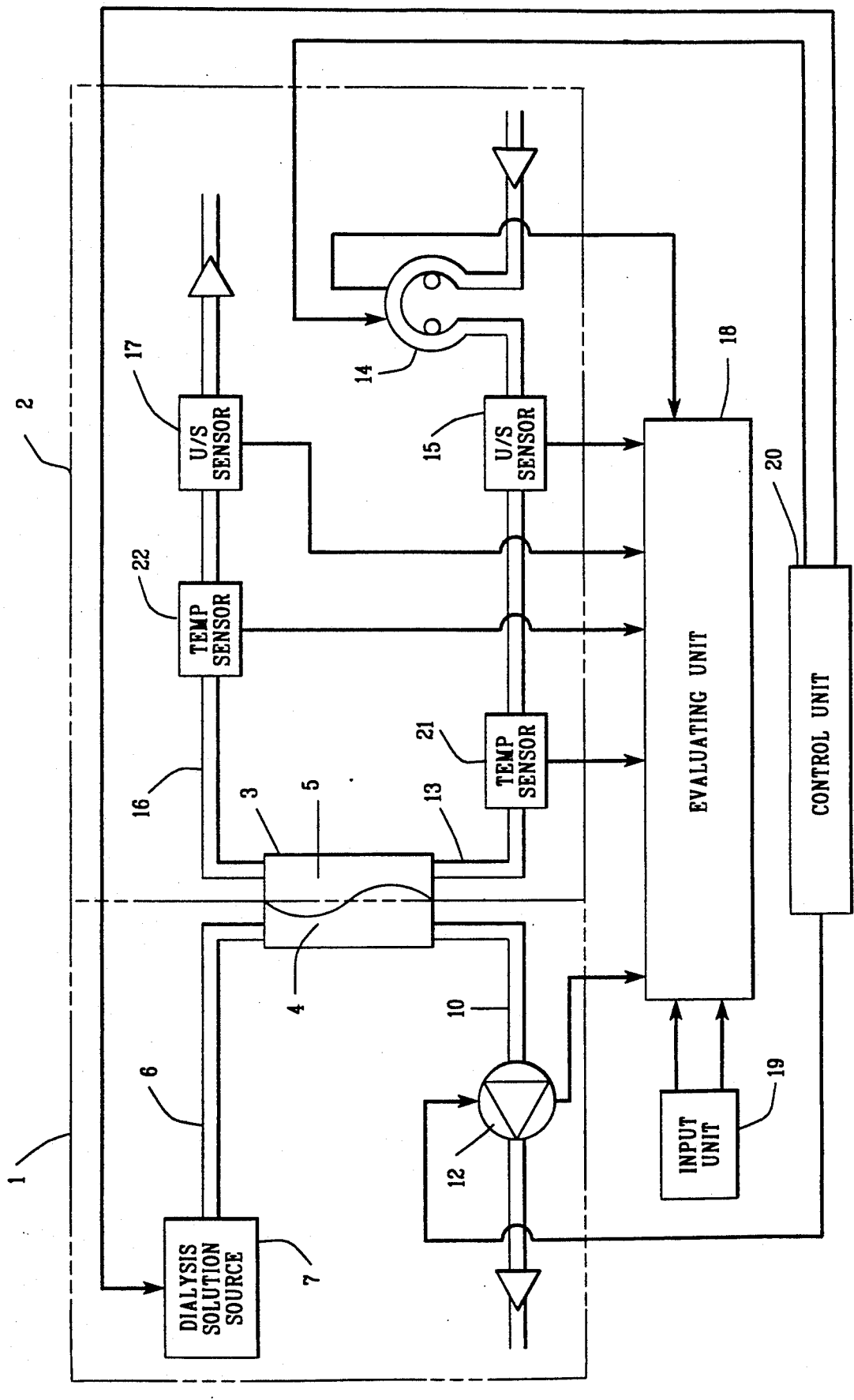

MEASURING THE CHANGE OF INTRAVASCULAR BLOOD VOLUME DURING BLOOD FILTRATION

CROSS REFERENCE TO RELATED APPLICATION

The present application is a continuation application of U.S. patent application Ser. No. 07/380,218, filed Jul. 14, 1989, now abandoned.

BACKGROUND OF THE INVENTION

1. Field of the Invention

The invention proceeds from an apparatus for measuring the change of the intravascular blood volume as is known from EP 0 089 003.

2. Description of the Related Art

In blood purifying methods in which a fluid exchange or a withdrawal of fluid is provided it is necessary to control this liquid or fluid exchange in such a manner that undesired negative effects on the health of the patient are avoided.

Methods in which this necessity exists are for example hemodialysis, hemofiltration and plasma filtration.

The removal of fluid excess from the body of the patient requires a very precise control of the fluid balance and for this reason dialysis methods can only be carried out with fluid-balancing means. In spite of this precise balancing dialysis-typical unpleasant effects still occur in patients, such as headache, vomiting and muscular cramps. The probable reason for this is the too rapid extraction of sodium ions from the blood due to the concentration difference of sodium in the blood (extracorporeal circuit) and in the dialysis solution and in the too rapid fluid withdrawal.

It is known in hemodialysis to carry out the so-called volumetric ultrafiltration control. The prior art of ultrafiltration control or monitoring in hemofiltration is the balancing of the ultrafiltrate and the substitution solution with the aid of one or two weighing devices or balances, cf. for example DE-OS 3,132,790. These methods, which have already been industrially employed, permit a fluid extraction in accordance with the direction of the physician or operator, i.e. in accordance with the input over a predetermined period of time, a certain amount of fluid is withdrawn from the patient. It is also known to prescribe a so-called "ultrafiltration profile", i.e. a time-dependent variation of the ultrafiltration rate. The objective of the variation of the ultrafiltration rate with time is the withdrawal of the predetermined ultrafiltration amount from the patient in the way causing the least possible detrimental effects, i.e. in particular avoiding blood pressure drops.

In addition, by entering physiological and treatment parameters into such apparatuses for carrying out the ultrafiltration the change of the intracellular and extracellular volume can be predicted. Since these changes considerably influence the health of the patient the operator of the apparatus attempts to configure the ultrafiltration profile in such a manner that as uniform as possible a decrease of the extracellular volume takes place. Although this has led to an improvement of the otherwise unsatisfactory treatment result in the case of patients where the adjustment is difficult, this procedure is too complicated for a routine method.

Aforementioned EP 0 089 003 discloses a blood purification apparatus in which in the extracorporeal blood circuit a hematocrit measuring device is arranged which is connected to a control and evaluating unit. This hematocrit measuring device is based on an electrical resistance measurement of the blood during the blood filtration. From the change of the resistance values of the blood the change of the hematocrit is determined and from the latter the intravascular blood volume is deduced. Such resistance measurements have however the disadvantage that the measured values are falsified by other influencing factors such as flow rate, erythrocyte orientation, etc.

In DE-OS 3,640,089, which is based on the principle known from EP 0 089 003, from the values obtained from a conductivity relative measuring arrangement and from the conductivity of the fresh dialysis solution and the blood flow, as well as the performance parameters of the dialyzer, the plasma conductivity and the change of the plasma and blood conductivity are determined. Thereafter the hematocrit is calculated during the dialysis and from the hematocrit the change in the intravascular blood volume is deduced and in dependence upon the change of the intravascular blood volume the ultrafiltration rate determined.

A further apparatus for measuring the conductivity is known from EP-0029793.

Other methods for blood volume variation measurement are described for example in:

R. N. Greenwood, C. Aldridge, W. R. Cattell, Clinical Science (1984) 66, 575–583: "Serial blood water estimations and in-line blood viscometry: the continuous measurement of blood volume during dialysis procedures"

and U. Schallenberg, S. Stiller, H. Mann, Life Support Systems (1987) 5, "A New Method of Continuous Haemoglobinometric Measurement of Blood Volume During Haemodialysis".

However of these known methods has so far led to industrial use because firstly there are difficult to surmount measuring and method problems and secondly complicated and additional apparatuses are necessary, such as conductivity measuring devices.

SUMMARY OF THE INVENTION

The object of the invention is therefore to provide an apparatus with which these disadvantages are avoided and with which the change of the intravascular blood volume during the filtration can be determined in simple manner.

The apparatus of the present invention comprises at least one ultrasonic sensor which is arranged in the extracorporeal blood circuit of the blood purifying apparatus and an evaluating unit which is connected to said ultrasonic sensor. The evaluating unit is constructed in such a manner that at the start of the filtration a first ultrasonic signal is stored and during the filtration the change of the ultrasonic signals is determined. From this change the variation of the hematocrit is determined and from the latter the change of the intravascular blood volume deduced.

The ultrasonic sensor may be installed into the extracorporeal blood circuit of a hemodialysis apparatus, a hemofiltration apparatus or a plasma filtration apparatus.

In the work by E. L. Bradley and Jose Sacerio ("The velocity of ultrasound in human blood under varying physiologic parameters", Journal of Surgical Research 12, 290–297, 1972) ultrasonic measurements on human blood are described and the relationships between the ultrasonic signals and the temperature, the hematocrit and the protein content explained. It is also apparent from this work that the measurements are made in the Megahertz range and it was found that the sound velocity is independent of the frequency.

In K. Kirk Shung ("Tissue Characterization with Ultrasound", Chapter 10, page 230, 1986) an empirical formula is given based on the work of Bradley and Sacerio. According to this formula the relationship between the sound velocity c in m/sec, the temperature T in °C., the hematocrit H in % and protein content w in g% is as follows:

$$c = 1482.26 + 1.54\,T + 0.51\,H + 2.8\,w \quad (1)$$

If the normal values specified by K. Kirk Shung are inserted the following is obtained $$c = 1482.26 + 56.98 + 20.4 + 16.8 \quad (2)$$

It is apparent from this that the hematocrit and the protein content enter in the same order of magnitude.

In the case of a hyperhydrated patient whose condition is to be corrected by ultrafiltration the two values change proportionally. The order of magnitude of this change is 10–20%, corresponding to a change of the sound velocity of 3–6 m/sec which in turn is equivalent to the velocity change caused by a temperature change of 2° C. This shows that as a rule, account must be taken of the temperature.

Consequently, if the temperature T is additionally measured information on the hematocrit can be derived from the measured sound velocity.

According to a particular embodiment of the apparatus according to the invention in the extracorporeal circuit at least one temperature measuring device is therefore arranged which is likewise connected to the evaluating unit which is constructed in such a manner that the hematocrit can be corrected with regard to the temperature.

If in this manner with the aid of the ultrasonic sensor before starting the treatment the hematocrit $H_o$ is measured and during the treatment the particular hematocrit H, then the change of the blood volume dV can be determined as follows:

$$\frac{dV}{V} = \frac{1 - H_o}{H} \quad (3)$$

The desired resolution of 1% change of the blood volume makes it necessary to measure a relative change of the ultrasonic velocity of about 0.4 m/sec. This is about 0.03% of the ultrasonic velocity in serum.

From this, the requirements of the size of the measuring path and the magnitude of the measuring frequency can be derived. For a travelling distance of 1 cm the travelling time is of the order of magnitude of 6 μsec and the desired resolution 2 nsec. This resolution lies within the range of that which can be achieved with conventional electronic circuits. To achieve this resolution in practice a frequency of the order of magnitude of 60 MHz or more is necessary. The estimation of the wavelength gives for 1 MHz a wavelength of 1.5 mm.

The blood density can be measured with an ultrasonic sensor which is arranged in the arterial part of the extracorporeal blood circuit.

To follow the relative change of the blood density during the blood purification in accordance with a further embodiment in the extracorporeal blood circuit two ultrasonic sensors are installed, one being arranged in the arterial part of the blood circuit and the second in the venous part of the blood circuit. Both the ultrasonic sensors are connected to the evaluating unit which is designed in such a manner that precisely this additional relative change of the ultrasonic signals during the filtration is detected and from it the relative change of the intravascular blood volume can be determined.

The advantage of the apparatus claimed further resides in that the ultrasonic sensors can be combined with the measurement of other parameters which are likewise measured with ultrasound, thus enabling the apparatus expenditure to be kept within limits.

Thus, according to a further embodiment the evaluating unit is equipped with a means for detecting air.

Furthermore, the ultrasonic sensor can be integrated into a drip chamber and the evaluating unit constructed for detecting the fluid level. Preferably, the drip chamber in this case is provided with a measuring mark which reflects ultrasonic waves and is arranged at a defined distance, i.e. unalterable during the measurement, beneath the fluid level to be expected. The signal transmitted by the transmitter is then reflected twice, once at the measuring mark and again at the fluid surface. From the first signal, if the spacing is known, the sonic velocity can be derived and from the result and the travelling time of the second signal the level of the fluid surface determined.

Furthermore, the apparatus can be combined with a Doppler flow measuring device. These possible combinations show that a change of the blood volume can be determined without great additional technical expenditure as was necessary in the prior art.

The ultrasonic sensor can be equipped in known manner with a transmitter and an oppositely disposed receiver but can also operate by employing the reflection. For this purpose the receiver is not arranged opposite but corresponding to the angle of reflection which may for example be $< 90°$ or $> 270°$. With a reflection angle of 180° the receiver is identical to the transmitter.

BRIEF DESCRIPTION OF THE DRAWING

Hereinafter an example of embodiment of the invention will be explained in detail with the aid of the drawing. In the FIGURE a hemodialysis apparatus is shown.

DESCRIPTION OF THE PREFERRED EMBODIMENTS

The hemodialysis apparatus consists essentially of a dialysis solution part 1 and an extracorporeal blood circuit 2 between which a dialyzer 3 is disposed which has a dialysis solution compartment 4 and a blood compartment 5. The dialysis solution compartment 4 is connected upstream of the dialyzer 3 via a dialysis solution conduit 6 to a dialysis solution source 7. Downstream of the dialyzer 3 the dialysis solution compartment 4 is followed by a further conduit 10 which has a dialysis solution pump 12.

In the extracorporeal blood circuit 2 in the blood conduit 13 upstream of the dialyzer 3 a first temperature measuring device 21 and a first ultrasonic sensor 15 are disposed.

Connected to the blood compartment 5 downstream of the dialyzer 3 is a further blood conduit 16 which additionally comprises a second ultrasonic sensor 17 and a further temperature measuring device 22. The latter temperature measuring device 22 is necessary to enable account to be taken of temperature losses occurring in the dialysis.

The dialysis solution pump 12 and the blood pump 14 as well as the ultrasonic sensors 15 and 17 and the temperature measuring devices 21 and 22 pass their delivery signals or measured values to an evaluating unit 18 in which the determination of the blood volume is carried out. The evaluating unit 18 is further connected to an input unit 19 and a control unit 20 which passes its signals to the dialysis solution mixing means 7, the dialysis solution pump 12 and the blood pump 14.

In the dialysis solution mixing means 7 a concentrate pump, not shown in detail, and a corresponding water inlet are arranged, the dialysis solution being made up in accordance with the output signal of the control unit 20.

By determining the change of the blood volume continuously during the treatment with the aid of the ultrasonic sensors 15 and 17 a continuous monitoring of the fluid amount extracted is possible. If deviations occur in the predetermined fluid extraction rate, which is entered via the input unit 19, the evaluating unit 18, taking account of the delivery rates of the pumps 14 and 12, determines whether these delivery rates must be changed or the dialysis solution mixing means driven differently. This is done by corresponding signals which are sent to the control unit 20.

I claim:

1. Apparatus for measuring the change in intravascular blood volume occurring during a blood filtration procedure by measuring the change of the hematocrit of the blood, said apparatus being adapted for use with a blood purification device in which the filtration procedure is carried out and which has an extracorporeal blood circuit connected to a patient, said apparatus comprising:
   a measuring device comprising ultrasonic sensor means adapted to be connected to the extracorporeal blood circuit of the device for ultrasonically examining the blood flowing in the circuit and for providing a signal indicative of the hematocritic properties thereof; and
   an evaluating unit coupled to said sensor means, said evaluating unit including means for receiving the signal from said ultrasonic sensor means, said evaluating unit including means for storing a signal from said ultrasonic sensor means obtained at the start of the blood filtration procedure, and said evaluating unit including means for determining the change in the signal from said ultrasonic sensor means occurring during the blood filtration procedure for determining the change in the hematocrit of the blood and thus the change in the intravascular blood volume.

2. The apparatus according to claim 1 wherein the extracorporeal blood circuit of the blood purification device has an arterial part for withdrawing blood from the patient and a venous part for returning blood to the patient and wherein said ultrasonic sensor means is further defined as means adapted to be connected to the arterial part of the extracorporeal blood circuit for ultrasonically examining the blood flowing in the arterial part of the extracorporeal blood circuit.

3. The apparatus according to claim 2 wherein said ultrasonic sensor means comprises first and second ultrasonic sensors, wherein said first ultrasonic sensor is adapted to be connected in the arterial part of the extracorporeal blood circuit for ultrasonically examining the blood flowing in the arterial part of the extracorporeal blood circuit, said first ultrasonic sensor being coupled to said evaluating unit for providing a signal indicative of the hematocritic properties of the blood flowing in the arterial part of the circuit to the evaluating unit, wherein said second ultrasonic sensor is adapted to be connected in the venous part of the extracorporeal blood circuit for ultrasonically examining the blood flowing in the venous part of the extracorporeal blood circuit, said second ultrasonic sensor being coupled to said evaluating unit for providing a signal indicative of the hematocritic properties of the blood flowing in the venous part of the circuit to the evaluating unit, and wherein said evaluating unit is further defined as including means for determining the relative change in the signals received from said first ultrasonic sensor and said second ultrasonic sensor occurring during a blood filtration procedure for determining the relative change of the hematocrit of the blood and thus the relative change in intravascular blood volume.

4. The apparatus according to claim 1 further including a temperature measuring device adapted to be connected to the extracorporeal blood circuit and coupled to said evaluating unit, said evaluating unit including means for correcting the determination of the hematocrit of the blood for temperature changes.

5. The apparatus according to claim 4 including a plurality of temperature measuring devices adapted to be connected to the extracorporeal blood circuit and coupled to said evaluating unit.

6. The apparatus according to claim 1 wherein the blood purification apparatus has a control unit for controlling the filtration procedure and wherein said evaluating unit is further defined as adapted to be connected to said control unit for providing an input signal thereto.

7. The apparatus according to claim 1 further including means for detecting air in the extracorporeal blood circuit, said air detecting means being connected to said evaluating unit.

8. The apparatus according to claim 1 wherein the extracorporeal blood circuit of the blood purification device has a drip chamber and wherein said ultrasonic sensor means is adapted to be connected to the drip chamber for providing a signal indicative of liquid levels in the drip chamber, said evaluating unit including means responsive to the liquid levels signal for determining liquid levels in the drip chamber.

9. The apparatus according to claim 1 wherein said apparatus further including a Doppler blood flow measuring device adapted to be connected to the extracorporeal blood circuit for measuring the flow properties of the blood in the extracorporeal blood circuit and for providing a signal in accordance therewith, said measuring device being coupled to said evaluating unit.

* * * * *

UNITED STATES PATENT AND TRADEMARK OFFICE
CERTIFICATE OF CORRECTION

PATENT NO. : 5,230,341

DATED : July 27, 1993

INVENTOR(S) : Hans-Dietrich Polaschegg

It is certified that error appears in the above-identified patent and that said Letters Patent is hereby corrected as shown below:

CLAIM 2, Col. 5, Line 62, delete "further defined as means"; CLAIM 6, Col. 6, Line 41, delete "further defined as"; CLAIM 7, Col. 6, Line 45, after the word "means" insert ---adapted---

Signed and Sealed this

Nineteenth Day of April, 1994

Attest:

BRUCE LEHMAN

Attesting Officer    Commissioner of Patents and Trademarks